United States Patent
Marhold et al.

(10) Patent No.: US 7,041,852 B2
(45) Date of Patent: May 9, 2006

(54) PERFLUOROALKYLANILINES

(75) Inventors: Albrecht Marhold, Leverkusen (DE); Axel Pleschke, Köln (DE)

(73) Assignee: Bayer Chemicals AG, Leverkusen (DE)

( * ) Notice: Subject to any disclaimer, the term of this patent is extended or adjusted under 35 U.S.C. 154(b) by 137 days.

(21) Appl. No.: 10/702,704

(22) Filed: Nov. 6, 2003

(65) Prior Publication Data

US 2004/0152898 A1 Aug. 5, 2004

(30) Foreign Application Priority Data

Nov. 11, 2002 (DE) ................................. 102 52 275

(51) Int. Cl.
*C07C 211/45* (2006.01)
*C07C 211/46* (2006.01)
(52) U.S. Cl. ........................ 564/442; 564/218; 564/412
(58) Field of Classification Search ................. 564/218, 564/412, 442
See application file for complete search history.

(56) References Cited

U.S. PATENT DOCUMENTS

| | | | |
|---|---|---|---|
| 4,731,450 A | 3/1988 | Wakselman et al. | 546/303 |
| 6,184,425 B1 | 2/2001 | Kolomeitsev et al. | 570/170 |
| 6,362,369 B1 | 3/2002 | Tohnishi et al. | 564/156 |
| 6,559,341 B1 | 5/2003 | Tohnishi et al. | 564/442 |
| 6,600,074 B1 | 7/2003 | Onishi et al. | 564/442 |
| 2001/0041814 A1 | 11/2001 | Tohnishi et al. | 564/156 |
| 2002/0198399 A1 | 12/2002 | Onishi et al. | 558/418 |
| 2003/0055287 A1 | 3/2003 | Tohnishi et al. | 564/154 |

FOREIGN PATENT DOCUMENTS

| | | |
|---|---|---|
| DE | 101 29 057 | 12/2002 |
| EP | 298 803 | 9/1991 |
| FR | 2660923 | 10/1991 |

OTHER PUBLICATIONS

Winey D.A. et al.: "Elimination mechanisms. Deuteroxide/Hydroxide isotope effects as a measure of proton transfer in the transition states for E2 elimination of 2-(p-trimethylammoniophenyl)ethyl 'onium ions and halides." Journal of the American Chemical Society., vol. 97, No. 11, 1975, pp. 3102-3108.

Zhou Q. L. et al.: "A facile method for fluoroalkylation of aniline and its derivatives" Journal of Fluorine Chemistry., vol. 39, No. 1, 1988, pp. 87-98.

Yagupol'Skii, L. M. et al: "Perfluoroalkylation of thiazole and pyridine derivatives" Journal of General Chemistry of the USSR, 39(9), 2041-44 ISSN: 0022-1279, 1969.

Journal of Fluorine Chemistry 111 (2001) 107-113, "Fluoroalkylation of aromatic compounds with per(poly)fluoroalkyl chlorides Initiated by sodium dithionite in DMSO", Xiao-Ting Huang, Zheng-Yu Long, Qing-Yun Chen.

*Primary Examiner*—Brian Davis
(74) *Attorney, Agent, or Firm*—Jennifer R. Song

(57) ABSTRACT

The present invention relates to a process for preparing perfluoroalkylanilines and to their use for preparing active ingredients, in particular for agrochemicals.

22 Claims, No Drawings

PERFLUOROALKYLANILINES

BACKGROUND OF THE INVENTION

1. Field of the Invention

The present invention relates to a process for preparing perfluoroalkylanilines and to their use for preparing active ingredients, in particular for agrochemicals.

2. Brief Description of the Prior Art

Perfluoroalkylanilines, in particular 4-perfluoroalkyl-2-methylanilines, are valuable starting materials for preparing insecticides of the aroylurea type (see also EP-A 919 542 and EP-A 936 212). Perfluoroalkylanilines can be prepared, for example, by reacting anilines with perfluoroalkyl iodides or bromides in aprotic solvents, either in the presence of metals and sulphur dioxide (EP-A 206 951 and FR-A 2 660 923) or in the presence of alkali metal dithionite (EP-A 298 803). In a similar manner, perfluoroalkyl chlorides can be reacted in dimethyl sulphoxide (Huang et al., J. Fluorine Chem., 111, 2001, 107–113). A disadvantage of the methods mentioned is that the perfluoroalkyl iodides or bromides are very expensive and only allow very low or only moderate yields to be achieved.

EP-A 1 006 102 discloses that perfluoroalkylanilines can be obtained by reacting anilines with perfluoroalkyl iodides in a biphasic system in the presence of a reducing agent. However, in this case also, the high cost of the perfluoroalkyl iodides is disadvantageous.

There is therefore a need to provide a process which enables the preparation of perfluoroalkylanilines in good yields and in a simple manner.

SUMMARY OF THE INVENTION

A process has now been found for preparing compounds of the formula (I)

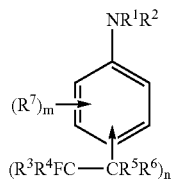

(I)

in which
$R^1$ and $R^2$ are each independently hydrogen, $C_1$–$C_{12}$-alkyl, $CO(C_1$–$C_{12}$-alkyl), $CO(C_5$–$C_{14}$-aryl), $CO(C_6$–$C_{15}$-arylalkyl), $COO(C_1$–$C_{12}$-alkyl), $COO(C_5$–$C_{14}$-aryl), $COO(C_6$–$C_{15}$-arylalkyl), $COO(C_2$–$C_{12}$-alkenyl) or $C_6$–$C_{15}$-arylalkyl, or
$NR^1R^2$ as a whole is a cyclic radical having a total of 4 to 16 carbon atoms, or is isocyanate, and
$R^3$, $R^4$, $R^5$ and $R^6$ are each fluorine or $C_1$–$C_{12}$-perfluoroalkyl, and/or in each case two of the $R^3$, $R^4$, $R^5$ and $R^6$ radicals each form a cyclic perfluoroalkyl radical having a total of 4 to 20 carbon atoms, and
n is one or two, and
$R^7$ is $C_1$–$C_{12}$-alkyl, $C_5$–$C_{14}$-aryl, $C_6$–$C_{15}$-arylalkyl, hydroxyl, chlorine, bromine, fluorine, nitro, cyano, free or protected formyl, $C_1$–$C_{12}$-haloalkyl, or radicals of the formulae (IIa) to (IIf), A-B-D-E (IIa)

A-E (IIb)

A-SO$_2$-E (IIc)

A-B—SO2R9 (IId)

A-SO$_3$W (IIe)

A-COW (IIf)

in which, each independently,
A is absent or is a C1–C8-alkylene radical and
B is absent or is oxygen, sulphur or $NR^8$,
where
$R^8$ is hydrogen, $C_1$–$C_8$-alkyl, $C_6$–$C_{15}$-arylalkyl or $C_5$–$C_{14}$-aryl, and
D is a carbonyl group and
E is $R^9$, $OR^9$, $NHR^{10}$ or $N(R^{10})_2$
where
$R^9$ is $C_1$–$C_8$-alkyl, $C_6$–$C_{15}$-arylalkyl, $C_1$–$C_8$-haloalkyl or $C_5$–$C_{14}$-aryl, and
$R^{10}$ is in each case independently $C_1$–$C_8$-alkyl, $C_6$–$C_{15}$-arylalkyl or $C_6$–$C_{14}$-aryl, or $N(R^{10})_2$ together is a cyclic amino radical having 4 to 12 carbon atoms and
W is OH, $NH_2$ or OM where M is an alkali metal ion, half an equivalent of an alkaline earth metal ion, an ammonium ion or an organic ammonium ion, or two $R^7$ radicals together may form a cyclic radical having a total of 5 to 12 carbon atoms, and
m is an integer from 0 to 5–n, which is characterized in that
compounds of the formula (II)

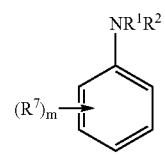

(II)

in which
$R^1$, $R^2$, $R^7$ and m are each as defined above
are reacted in a step a)
with compounds of the formula (III)

$R^3R^4Hal^1C$—$CHal^2R^5R^6$ (III)

in which
$R^3$, $R^4$, $R^5$ and $R^6$ are each as defined above, and
$Hal^1$ and $Hal^2$ are each independently chlorine, bromine or iodine, preferably identically chlorine or bromine and more preferably identically bromine,
to give compounds of the formula (IV)

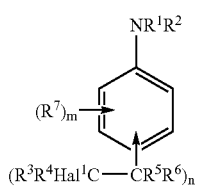

(IV)

in which
$R^1$, $R^2$, $R^3$, $R^4$, $R^5$, $R^6$ and $R^7$, and also m, n and $Hal^1$, are each as defined above and
in a step b),
the compounds of the formula (IV) are converted to compounds of the formula (I) by reacting with ionic fluoride.

For the purposes of the invention, all radical definitions, parameters and illustrations hereinabove and listed hereinbelow, in general or within areas of preference, i.e. the particular ranges and preferred ranges, may be combined as desired.

DETAILED DESCRIPTION OF THE INVENTION

The invention is described more fully hereunder with particular reference but without limitation to the preferred embodiments. Alkyl, alkylene, alkoxy and alkenyl are each independently a straight-chain, cyclic, branched or unbranched alkyl, alkylene, alkoxy or alkenyl radical respectively. The same applies to a nonaromatic moiety of an arylalkyl radical.

$C_1$–$C_4$-Alkyl is, for example, methyl, ethyl, n-propyl, isopropyl, n-butyl, sec-butyl and tert-butyl, $C_1$–$C_8$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-ethyl-2-methylpropyl, n-heptyl and n-octyl, and $C_1$–$C_{12}$-alkyl is still further additionally, for example, adamantyl, n-nonyl, n-decyl and n-dodecyl.

$C_1$–$C_4$-Alkoxy is, for example, methoxy, ethoxy, n-propoxy, isopropoxy, n-butoxy, sec-butoxy and tert-butoxy.

$C_2$–$C_{12}$-Alkenyl is, for example, vinyl, 1-propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 1-heptenyl, 1-octenyl or 2-octenyl.

Perfluoroalkyl is in each case independently a straight-chain, cyclic, branched or unbranched alkyl radical which is fully substituted by fluorine atoms.

For example and with preference, $C_1$–$C_4$-perfluoroalkyl is trifluoromethyl, pentafluoroethyl, heptafluoroisopropyl and n-nonafluorobutyl, and $C_1$–$C_{12}$-perfluoroalkyl is further additionally, for example, perfluorocyclopentyl, perfluorocyclohexyl and perfluorododecyl.

Aryl is in each case independently a heteroaromatic radical having 5 to 18 framework carbon atoms of which no, one, two or three framework carbon atoms per cycle, but at least one framework carbon atom in the entire molecule may be substituted by heteroatoms selected from the group of nitrogen, sulphur and oxygen, but is preferably a carbocyclic aromatic radical having 6 to 18 framework carbon atoms.

Examples of carbocyclic aromatic radicals having 6 to 18 framework carbon atoms are phenyl, naphthyl, phenanthrenyl, anthracenyl or fluorenyl; heteroaromatic radicals having 5 to 18 framework carbon atoms of which no, one, two or three framework carbon atoms per cycle, but at least one framework carbon atom in the entire molecule, may be substituted by heteroatoms selected from the group of nitrogen, sulphur or oxygen are, for example, pyridinyl, oxazolyl, benzofuranyl, dibenzofiranyl or quinolinyl.

The carbocyclic aromatic radical or heteroaromatic radical may also be substituted by up to five identical or different substituents per cycle which are selected from the group of chlorine, fluorine, $C_1$–$C_{12}$-alkyl, $C_1$–$C_{12}$-perfluoroalkyl, COO($C_1$–$C_8$-alkyl), CON($C_1$–$C_8$-alkyl)$_2$, COO($C_1$–$C_8$-arylalkyl), COO($C_4$–$C_{14}$-aryl), CO($C_1$–$C_8$-alkyl), $C_5$–$C_{15}$-arylalkyl or tri($C_1$–$C_6$-alkyl)siloxyl.

Arylalkyl is in each case independently a straight-chain, cyclic, branched or unbranched alkyl radical which may be singly, multiply or fully substituted by aryl radicals as defined above.

$C_6$–$C_{15}$-Arylalkyl is, for example and with preference, benzyl.

The preferred substitution patterns for compounds of the formula (I) are defined hereinbelow:

$R^1$ and $R^2$ are preferably each identically hydrogen or $NR^1R^2$ as a whole is $NHCO(C_1$–$C_{12}$-alkyl), $NHCO(C_5$–$C_{14}$-aryl) or $NHCO(C_6$–$C_{15}$-arylalkyl) or isocyanate.

$NR^1R^2$ as a whole is more preferably $NH_2$ or $NHCOCH_3$.

$R^3R^4FC$—$CR^5R^6$ as a whole is preferably a secondary $C_3$–$C_{12}$-perfluoroalkyl radical, more preferably, as a whole, heptafluoro-2-propyl, perfluorocyclobutyl, perfluorocyclopentyl or perfluorocyclohexyl.

Most preferably, $R^3R^4FC$—$CR^5R^6$ as a whole is heptafluoro-2-propyl.

n is preferably 1.

$R^7$ is preferably in each case independently $C_1$–$C_4$-alkyl, chlorine, fluorine, nitro, cyano or $C_1$–$C_4$-alkoxy, more preferably methyl, ethyl, methoxy or ethoxy, most preferably methyl.

m is preferably 0, 1 or 2, more preferably 0 or 1.

A particularly preferred compound of the formula (I) is 2-methyl-4-(heptafluoro-2-propyl)aniline.

The compounds of the formula (III) used as starting materials are known from the literature or can be synthesized in a similar manner to the literature. In a particularly preferred embodiment, the compounds of the formula (III) are prepared by reacting compounds of the formula (V)

$$R^3\text{—}CR^4\text{=}CR^5\text{—}R^6 \qquad (V)$$

with halogen compounds of the formula (VI)

$$Hal^1\text{-}Hal^2 \qquad (VI).$$

In the formulae (V) and (VI), $R^3$, $R^4$, $R^5$ and $R^6$ and also $Hal^1$ and $Hal^2$, each have the definitions and areas of preference specified above under the formulae (I) and (III).

Particularly preferred compounds at the formula (III) include:

1,2-dibromo-1,1,2,3,3,3-hexafluoropropane, 2,3-dibromo-1,1,1,2,3,4,4,4-octafluorobutane, 1,2-dichloro-1,2,3,3,4,4-tetrafluorocyclobutane and 1,2-dibromo-1,2,3,3,4,4,5,5-octafluorocyclopentane, and very particular preference is given to 1,2-dibromo-1,1,2,3,3,3-hexafluoropropane.

In step a), compounds of the formula (II) are reacted with compounds of the formula (III) to give compounds of the formula (IV).

The molar ratio per equivalent of n of compounds of the formula (III) to compounds of the formula (II) may be, for example, 0.7 to 1.8, preferably 0.9 to 1.2 and more preferably 1.0 to 1.1.

The compounds of the formula (IV) are likewise encompasssed by the invention as particularly valuable intermediates. The areas of preference for the moieties the compounds of formula (IV) are the same as for the formulae (I) and (III).

Individual compounds of the formula (IV) include:
4-(1-Bromo-1,1,2,3,3,3-hexafluoro-2-propyl)aniline, 2-methyl-4-(1-bromo-1,1,2,3,3,3-hexafluoro-2-propyl)aniline, 2-fluoro-4-(1-bromo-1,1,2,3,3,3-hexafluoro-2-propyl) aniline, 2-chloro-4-(1-bromo-1,1,2,3,3,3-hexafluoro-2-propyl)aniline, 2-bromo-4-(1-bromo-1,1,2,3,3,3-hexafluoro-2-propyl)aniline, 2-methyl-4-(2-bromotetrafluoroethyl)aniline, 2-methyl-4-(1-bromo-1,1,2,3,3,3-hexafluoro-2-propyl)acetanilide, 2-methyl-4-(2-bromo-1,1,1,2,3,4,4,4-octafluoro-3-butyl)aniline and 2-methyl-4-(2-bromo-2,3,3,4,4,5,5-octafluorocyclo-1-pentyl)aniline.

The reaction in step a) is preferably effected in the presence of a reducing agent and/or in the presence of light having a wavelength of 400 nm or less.

Suitable reducing agents are, for example: sulphur compounds in the averaged formal oxidation states +III, +IV and +V, optionally in a mixture with a metal, which has a standard reduction potential of 0 V or less.

Such sulphur compounds are, for example, alkali metal dithionites, such as sodium dithionite and potassium dithionite, or sulphur dioxide.

Suitable metals are, for example, manganese, zinc or aluminium.

Particularly suitable light sources which generate light having a wavelength of 400 nm or less are all customary UV lamps, in particular mercury vapour lamps.

Particular preference is given to carrying out step a) in the presence of alkali metal dithioniate, very particularly preferably sodium dithionite.

Typically, step a) is carried out in a liquid reaction medium.

Suitable for this purpose are, for example, polar organic solvents having a dipole moment [μ/D] of at least 2.8 and optionally with the addition of water, and also multiphasic reaction media having one aqueous and at least one organic phase.

Particularly suitable polar organic solvents are nitriles, for example acetonitrile, sulphoxides, for example dimethyl sulphoxide, sulphones, for example tetramethylene sulphone, and amidic solvents, for example dimethylformamide, N-methylpyrrolidone and N-methylcaprolactam.

Particularly suitable organic solvents for multiphasic reaction media are, for example, aliphatic or aromatic, optionally halogenated hydrocarbons, for example benzine fractions, benzene, toluene, xylene, chlorobenzene, dichlorobenzene, petroleum ether, hexane, cyclohexane, dichloromethane, chloroform or carbon tetrachloride, ethers, for example diethyl ether, diisopropyl ether, tert-butyl methyl ether, ketones, for example cyclohexanone, butanone or methyl isobutyl ketone, and esters, for example methyl acetate or ethyl acetate.

In a preferred embodiment of the process according to the invention, the reaction is carried out in a multiphasic reaction medium which has one aqueous and at least one organic phase, more preferably exactly one organic phase.

In these cases, preference is given to carrying out the reaction in the presence of phase transfer catalysts.

Suitable phase transfer catalysts are, for example, crown ethers such as 18-crown-6, 12-crown-4, dibenzo-18-crown-6 or dibenzo-12-crown-4, cryptands such as cryptand [2.2.2] or podands such as polyglycol ethers or those of the formula (VII),

(VII)

in which
(cation$^+$) is a substituted quaternary ammonium or phosphonium cation and
(anion$^-$) is the anion of an organic or inorganic acid.

Preferred phase transfer catalysts are those of the formula (VII) in which (cation$^+$) is a cation of the formula (VIII)

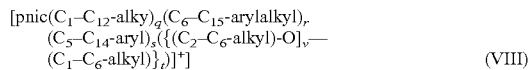

(VIII)

in which
pnic is nitrogen or phosphorus and
in which in each case (q+r+s+t)=4.

(Anion$^-$) is preferably fluoride, chloride, bromide, iodide, acetate, nitrate, sulphate, hydrogensulphate, tetrafluoroborate, hexafluorophosphate, tosylate and triflate, more preferably chloride, bromide, iodide, sulphate and hydrogensulphate.

Particularly preferred phase transfer catalysts are tetra-n-butylammonium iodide, tetra-n-butylammonium bromide, tetra-n-butylammonium chloride, tri-n-butyl-methylphosphonium bromide, tetra-n-butylammonium hydrogensulphate, trimethyl-$C_{13}/C_{15}$-alkylammonium chloride, trimethyl-$C_{13}/C_{15}$-alkylammonium bromide, dibenzyldimethylammonium methylsulphate, dimethyl-$C_{12}/C_{14}$-alkylbenzylammonium chloride, dimethyl-$C_{12}/C_{14}$-alkylbenzylammonium bromide, triethylbenzylammonium chloride, methyltrioctylammonium chloride, trimethylbenzylammonium chloride, tetrakisdiethylaminophosphonium chloride, bromide or iodide, and also tris-[2-(2-methoxyethoxy)ethyl]amine, and very particular preference is given to tetra-n-butylammonium hydrogensulphate.

The reaction temperature in step a) may be, for example, −10° C. up to the boiling point of the reaction medium under reaction pressure, but a maximum of 200° C., and preference is given to a reaction temperature of 0 to 70° C.

The reaction pressure in step a) may be, for example, 0.5 to 100 bar, preferably ambient pressure.

Preference is given to carrying out step a) also in the presence of a base. Suitable bases are, for example, alkaline earth metal or alkali metal hydroxides, acetates, phosphates, hydrogenphosphates, carbonates or hydrogencarbonates, for example sodium hydroxide, potassium hydroxide, sodium acetate, potassium acetate, calcium acetate, sodium carbonate, potassium carbonate, potassium hydrogencarbonate or sodium hydrogencarbonate, ammonium salts, for example ammonium acetate and ammonium carbonate, amines, for example trimethylamine, triethylamine, tributylamine, diisopropylethylamine, tetramethylguanidine, N,N-dimethylaniline, diazabicyclooctane (DABCO), diazabicyclononene (DBN), diazabicycloundecene (DBU), N-methylpiperidine and piperidine, or aromatic nitrogen compounds, for example pyridine, 2-, 3- and 4-N,N-dimethylaminopyridine, and even greater preference is given to alkali metal carbonates and hydrogencarbonates.

Preference is given to isolating compounds of the formula (IV) from the reaction mixture obtained from step a). This may be effected in a manner known per se by extractive processes with optional subsequent purifying operations such as distillation or recrystallization.

When compounds of the formula (IV) in which the ortho-position to the amino group is substituted by chlorine or bromine are to be used for subsequent step b), it is advantageous to initially subject the corresponding compound unsubstituted in the ortho-position to step a), and to carry out a halogenation before step b).

The halogenation may be effected in a manner known per se, and preference is given to the reaction with N-halosuccinimides in nitrites, for example acetonitrile.

In step b), the compounds of the formula (IV) are reacted with ionic fluoride to give compounds of the formula (I).

Ionic fluorides are, for example, quaternary ammonium fluorides or phosphonium fluorides, and also alkali metal fluorides or mixtures of the compounds mentioned. Examples of ammonium fluorides or phosphonium fluorides are those of the formula (IX)

(IX)

in which (cation$^+$) is as defined under the formula (VII), including its areas of preference.

Optionally, mixtures of phase transfer catalysts as defined above and/or halex catalysts with alkali metal fluorides can also be used.

Halex catalysts are, for example, tetrakis(dialkylamino) phosphonium compounds (WO 98/05610) or compounds of the formula (X)

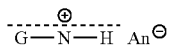   (X)

in which
G is a radical of the formulae (XIa) or (XIb)

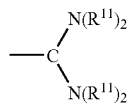   (XIa)

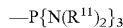   (XIb)

and
H, independently of G, is a radical of the formulae (XIa), (XIb), (XIc) or (XId)

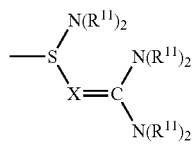   (XIc)

   (XId)

where
the $R^{11}$ radicals are each independently $C_1$–$C_{12}$-alkyl, $C_2$–$C_{10}$-alkenyl or $C_6$–$C_{12}$-aryl, or
$N(R^{11})_2$ as a whole is a 3- to 5-membered, saturated or unsaturated ring, or
the radicals of the formula (XIa) and/or the group

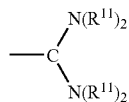

as a whole may each be a saturated or unsaturated, 4- to 8-membered ring, and
X is nitrogen or phosphorus and
An. is one equivalent of an anion, for example and with preference chloride, bromide, $(CH_3)_3SiF_2$, $HF_2$, $H_2F_2$, tetrafluoroborate, hexafluorophosphate, carbonate or sulphate.

The compounds of the formula (X) are obtainable, for example, by reacting compounds of the formula (XII)

[G-An']An.   (XII)

in which
G and An. are each as defined in formula (X) and
An' is chlorine or bromine with compounds of the formula (XIII)

   (XIII)

in which
G', with regard to the arrangement of the atoms, is as defined for G in formula (X), but is divalent, and the reaction is effected in the presence of a base.

The compounds of the formula (X) are described in DE 101 29 057.

However, preference is given to using alkali metal fluorides without phase transfer catalysts and/or halex catalysts for step b).

Preferred alkali metal fluorides are sodium fluoride, potassium fluoride and caesium fluoride or mixtures thereof, and particular preference is given to potassium fluoride.

Preference is given to using potassium fluoride which has a water content of 0.5% by weight or less, preferably 0.05% by weight or less, and an average particle size, based on the weight, of 200 μm or less.

The molar ratio of ionic fluoride to compound of the formula (IV) used may be, for example, 0.7 to 5, preferably 0.9 to 2 and more preferably 1.1 to 1.7. The amount of ionic fluoride in principle has no upper limit, but larger amounts are uneconomic.

Preference is given to carrying out step b) in the presence of organic solvents. Suitable organic solvents are, for example: ketones such as acetone, 2-butanone or methyl isobutyl ketone; nitrites, for example acetonitrile, propionitrile, benzonitrile, benzyl nitrile or butyronitrile; amides, for example N,N-dimethylformamide, N,N-dimethylacetamide, N-methylformanilide, N-methylpyrrolidone, N-methylcaprolactam or hexamethylphosphoramide; sulphoxides, for example dimethyl sulphoxide, sulphones, for example tetramethylenesulphone, polyethers, for example 1,4-dioxane, ethylene glycol dimethyl ether, ethylene glycol diethyl ether, diethylene glycol dimethyl ether or diethylene glycol diethyl ether, or mixtures of such organic solvents.

The maximum water content of the solvent in step b) is preferably 1% by weight, more preferably 0.2% by weight. Preference is given to attaining such a water content by incipient distillation or drying in a manner known per se. When alkali metal fluorides are used, particular preference is given to drying or incipiently distilling the solvent in the simultaneous presence of the alkali metal fluoride used.

The reaction temperature in step b) may be, for example, 60° C. up to the boiling point of the solvent used at reaction pressure, but a maximum of 300° C., preferably 110° C. up to the boiling point of the solvent used at reaction pressure, but a maximum of 200° C.

The reaction pressure in step b) may be, for example, 0.5 to 100 bar, preferably 3 to 25 bar.

The reaction time in step b) may be, for example, 10 min to 72 hours, preferably 2 to 12 hours.

The compounds of the formula (I) can be worked up in a manner known per se, typically, for example, by fractional distillation directly from the reaction mixture, optionally under reduced pressure.

The compounds of the formula (I) obtainable in accordance with the invention are suitable in particular in a process for preparing active ingredients in agrochemicals, for example insecticides of the aroylurea type.

A significant advantage of the compounds of the formula (I) obtainable in accordance with the invention is that they can be prepared in a simple manner in high yields from readily available reactants.

The invention is further described by the following illustrative but non-limiting examples.

EXAMPLES

Example 1

Preparation of 1,2-dibromohexafluoropropane 2357 g of bromine (760 ml, 14.75 mol) were initially charged at room temperature and hexafluoropropene was introduced with constant stirring until decolorization (19 hours, 2400 g, 16.00 mol). The reaction mixture was purged with nitrogen. In this way, 4710 g of 1,2-dibromohexafluoropropane (95% of theory) were obtained.

Example 2

Preparation of 2-methyl-4-(1-bromo-1,1,2,3,3,3-hexafluoro-2-propyl)aniline

First 154.36 g (0.887 mol) of sodium dithionite and then 50 g (0.467 mol) of o-toluidine (2-methylaniline) were added at room temperature to a mixture of 900 ml of water, 350 ml of tert-butyl methyl ether, 74.48 g (0.887 mol) of sodium hydrogencarbonate and 12.68 g of tetra-n-butylammonium hydrogensulphate. Subsequently, a solution of 274.684 g of 1,2-dibromo-1,1,2,3,3,3-hexafluoropropane in 100 ml of tert-butyl methyl ether was added dropwise at 35–40° C. and, on completion of addition, the mixture was stirred at 40° C. for a further 18 h. If necessary, sodium carbonate was used to adjust to a pH of 5 and the organic phase was removed, dried and concentrated. The remaining residue is incipiently distilled under reduced pressure at 0.3 mbar up to an internal temperature of 100° C.

In this way, 82 g (53% of theory) of the product were obtained.

Example 3

Preparation of 2-methyl-4-(heptafluoro-2-propyl)acetanilide 10 g (26.5 mmol) of 2-methyl-4-(1-bromo-1,1,2,3,3,3-hexafluoro-2-propyl)-acetanilide and 3 g (53 mmol) of calcined potassium fluoride are added to 100 ml of NMP. The suspension is heated to 175° C. in a pressure vessel under 3 bar of nitrogen with stirring for 4 h. NMP is distilled off under reduced pressure as far as possible, and the residue is added to 50 ml of water and extracted three times with dichloromethane. This gives a product mixture of 2-methyl-4-(heptafluoro-2-propyl)-acetanilide and 2-methyl-4-(1-bromo-1,1,2,3,3,3-hexafluoro-2-propyl)acetanilide.

Example 4

Preparation of 2-methyl-4-(2-bromotetrafluoroethyl)aniline

First 162.5 g (0.93 mol) of sodium dithionite and then 50 g (0.47 mol) of o-toluidine (2-methylaniline) and 242.47 g (0.47 mol) of 1,2-dibromotetrafluoroethane were added at room temperature to a mixture of 700 ml of water, 350 ml of tert-butyl methyl ether, 78.4 g (0.93 mol) of sodium hydrogencarbonate and 38 g of tetra-n-butylammonium hydrogensulphate. The mixture was stirred at room temperature for a further 24 h. If necessary, the pH was adjusted to approx. 5 using sodium carbonate, and the organic phase was removed, dried and concentrated.

This gave 104 g (78% of theory) of a product mixture having the composition 71% 4-(2-bromotetrafluoroethyl)-2-methylaniline, 13% 2-(2-bromotetrafluoroethyl)-6-methylaniline and 16% 2,4-di(2-bromotetrafluoroethyl)-6-methylaniline.

Example 5

Preparation of 4-(1-bromo-1,1,2,3,3,3-hexafluoro-2-propyl)aniline

First 476.74 g (2.74 mol) of sodium dithionite and then 250 g (2.68 mol) of aniline were added at room temperature to a mixture of 4000 ml of water, 1200 ml of tert-butyl methyl ether, 270.61 g (3.22 mol) of sodium hydrogencarbonate and 10.94 g of tetra-n-butylammonium hydrogensulphate. Subsequently, a solution of 998.07 g of 1,2-dibromo-1,1,2,3,3,3-hexafluoropropane in 300 ml of tert-butyl methyl ether was added dropwise at 35–40° C. and, on completion of addition, the mixture was stirred at RT for a further 18 h. If necessary, sodium carbonate was used to adjust to a pH of 5 and the organic phase was removed, dried and concentrated. The remaining residue is incipiently distilled under reduced pressure at 0.3 mbar up to an internal temperature of 100° C.

In this way, 644 g (65% of theory) of the product were obtained.

Example 6

Preparation of 2-chloro-4-(1-bromo-1,1,2,3,3,3-hexafluoro-2-propyl)aniline 18.24 g (0.14 mol) of N-chlorosuccinimide were added at 60° C. to a mixture of 40.0 g (0.12 mol) of 4-(1-bromo-1,1,2,3,3,3-hexafluoro-2-propyl)aniline from Example 6 and 125 ml of acetonitrile, and the resulting mixture was heated to reflux for 3 hours. Subsequently, the solvent was for the most part distilled off, the residue was washed with 100 ml of 1N NaOH solution, the organic phase was dried over sodium sulphate and finally the remaining solvent was removed under reduced pressure.

In this way, 41 g (81% of theory) of the product were obtained.

Example 7

Preparation of 2-bromo-4-(1-bromo-1,1,2,3,3,3-hexafluoro-2-propyl)aniline 22.11 g (0.12 mol) of N-bromosuccinimide were added at 60° C. to a mixture of 40.0 g (0.12 mol) of 4-(1-bromo-1,1,2,3,3,3-hexafluoro-2-propyl)aniline from Example 6 and 125 ml of acetonitrile, and the resulting mixture was heated to reflux for 3 hours. Subsequently, the solvent was for the most part distilled off, the residue was washed with 100 ml of 1N NaOH solution, the organic phase was dried over sodium sulphate and finally the remaining solvent was removed under reduced pressure.

In this way, 47 g (71% of theory) of the product were obtained.

Example 8

Preparation of 2-fluoro-4-(1-bromo-1,1,2,3,3,3-hexafluoro-2-propyl)aniline

First 195.86 g (1.12 mol) of sodium dithionite and then 50 g (0.45 mol) of 2-fluoroaniline were added at room temperature to a mixture of 450 ml of water, 225 ml of tert-butyl methyl ether, 94.50 (1.12 mol) of sodium hydrogencarbonate and 18.33 g of tetra-n-butylammonium hydrogensulphate. Subsequently, a solution of 348.54 g of 1,2-dibromo-1,1,2,3,3,3-hexafluoropropane in 200 ml of tert-butyl methyl ether was added dropwise at 35–40° C. and, on completion of addition, the mixture was stirred at RT overnight. Sodium carbonate was used to adjust to a pH of 5 and the organic phase was removed, dried and concentrated.

In this way, 25 g (14% of theory) of the product were obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing compounds of the formula (I)

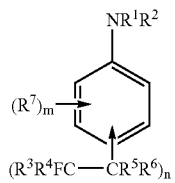

(I)

in which
   $R^1$ and $R^2$ are each independently hydrogen, $C_1$–$C_{12}$-alkyl, $CO(C_1$–$C_{12}$-alkyl), $CO(C_5$–$C_{14}$-aryl), $CO(C_6$–$C_{15}$-arylalkyl), $COO(C_1$–$C_{12}$-alkyl), $COO(C_5$–$C_{14}$-aryl) $COO(C_6$–$C_{15}$-arylalkyl), $COO(C_2$–$C_{12}$-alkenyl) or $C_6$–$C_{15}$-arylalkyl, or
   $NR^1R^2$ as a whole is a cyclic radical having a total of 4 to 16 carbon atoms, or is isocyanate, and
   $R^3$, $R^4$, $R^5$ and $R^6$ are each fluorine or $C^1$–$C^{12}$-pefluoroalkyl, or two of the $R^3$, $R^4$, $R^5$ and $R^6$ radicals form a cyclic perfluoroalkyl radical having a total of 4 to 20 carbon atoms, and
   n is one or two, and
   $R^7$ is $C_1$–$C_{12}$-alkyl, $C_5$–$C_{14}$-aryl, $C_6$–$C_{15}$-arylalkyl, hydroxyl, chlorine, bromine, fluorine, nitro, cyano, free or protected formyl, $C^1$–$C_{12}$-haloalkyl, or radicals of the formulae (IIa) to (IIf), A-B-D-E (IIa)

A-E (IIb)

A-SO$_2$-E (IIc)

A-B—SO$_2$R$^9$ (IId)

A-SO$_3$W (IIe)

A-COW (IIf)

in which, each independently,
   A is absent or is a $C_1$–$C_8$-alkylene radical and
   B is absent or is oxygen, sulphur or $NR^8$,
      where
      $R^8$ is hydrogen, $C_1$–$C_8$-alkyl, $C_6$–$C_{15}$-arylalkyl or $C_5$–$C_{14}$-aryl, and
   D is a carbonyl group and
   E is $R^9$, $OR^9$, $NHR^{10}$ or $N(R^{10})_2$
      where
      $R^9$ is $C_1$–$C_8$-alkyl, $C_6$–$C_{15}$-arylalkyl, $C_1$–$C_8$-haloalkyl or $C_5$–$C_{14}$-aryl, and
      $R^{10}$ is in each case independently $C_1$–$C_8$-alkyl, $C_6$–$C_{15}$-arylalkyl or $C_6$–$C_{14}$-aryl, or $N(R^{10})_2$ together is a cyclic amino radical having 4 to 12 carbon atoms and
   W is OH, $NH_2$ or OM where M is an alkali metal ion, half an equivalent of an alkaline earth metal ion, an ammonium ion or an organic ammonium ion, and
   m is an integer from 0 to 5–n,
comprising reacting: in step (a):
compounds of the formula (II)

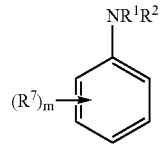

(II)

in which
   $R^1$, $R^2$, $R^7$ and m are each as defined above
with compounds of the formula (III)

$R^3R^4Hal^1C$—$CHal^2R^5R^6$ (III)

in which
   $R^3$, $R^4$, $R^5$ and $R^6$ are each as defined above and
   $Hal^1$ and $Hal^2$ are each independently chlorine, bromine or iodine,
to give compounds of the formula (IV)

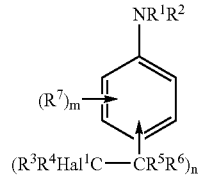

(IV)

in which
   $R^1$, $R^2$, $R^3$, $R^4$, $R^5$, $R^6$, $R^7$, m, n and $Hal^1$, are each as defined above and
in a step b),
converting the compounds of the formula (IV) to compounds of the formula (I) by reading with ionic fluoride.

2. Process according to claim 1, characterized in that $R^1$ and $R^2$ are identically hydrogen or $NR^1R^2$ as a whole is $NHCO(C_1$–$C_{12}$-alkyl), $NHCO(C_5$–$C_{14}$-aryl) or $NHCO(C_6$–$C_{15}$-arylalkyl).

3. Process according to claim 1, characterized in that $R^3R^4FC$—$CR^5R^6$ as a whole is a secondary $C_3$–$C_{12}$-perfluoroalkyl radical.

4. Process according to claim 1, characterized in that $R^7$ is in each case independently $C_1$–$C_4$-alkyl, chlorine, fluorine, nitro, cyano or $C_1$–$C_4$-alkoxy.

5. Process according to claim 1, characterized in that n is 1 and m is 0, 1 or 2.

6. Process according to claim 1, characterized in that 2-methyl-4-(heptafluoro-2-propyl)aniline is prepared.

7. Process according to claim 1, characterized in that the compounds of the formula (III) are converted by reacting compounds of the formula (V)

$$R^3—CR^4=CR^5—R^6 \quad (V)$$

with halogen compounds of the formula (VI)

$$Hal^1-Hal^2 \quad (VI)$$

where $R^3$, $R^4$, $R^5$, $R^6$, $Hal^1$ and $Hal^2$, are each as defined under formulae (I) and (III).

8. Process according to claim 1, characterized in that the compounds of the formula (III) used are 1,2-dibromo-1,1,2,3,3,3-hexafluoropropane, 2,3-dibromo-1,1,1,2,3,4,4,4-octafluorobutane, 1,2-dichloro-1,2,3,3,4,4-tetrafluorocyclobutane or 1,2-dibromo-1,2,3,3,4,4,5,5-octafluorocyclopentane.

9. Process according to claim 1, characterized in that the reaction in step a) is effected in the presence of a reducing agent and/or in the presence of light having a wavelength of 400 nm or less.

10. Process according to claim 9, characterized in that the reducing agents used are alkali metal dithionites.

11. Process according to claim 1, characterized in that the reaction is carried out in a multiphase reaction medium which has one aqueous and at least one organic phase.

12. Process according to claim 1, characterized in that the reaction in step a) is carried out in the presence of a phase transfer catalyst.

13. Process according to claim 1, characterized in that the reaction temperature in step a) is −10° C. up to the boiling point of the reaction medium under reaction pressure, and the reaction pressure is 0.5 to 100 bar.

14. Process according to claim 1, characterized in that step a) is carried out in the presence of a base.

15. Process according to claim 1, wherein compounds of the formula (IV) which bear chlorine or bromine in the ortho-position to the amino group further comprise the steps of reacting the compounds which are unsubstituted in the ortho position in step a) and halogenating to introduce these substituents in the ortho position prior to step b).

16. Process according to claim 1, characterized in that the ionic fluorides used in step b) are quaternary ammonium fluorides, phosphonium fluorides, or alkali metal fluorides or mixtures thereof or mixtures of phase transfer catalysts and/or halex catalysts with alkali metal fluorides.

17. Process according to claim 1, characterized in that sodium fluoride, potassium fluoride and caesium fluoride or mixtures thereof are used in step b).

18. Process according to claim 1, characterized in that step b) is carried out in the presence of organic solvent.

19. Process according to claim 18, characterized in that maximum water content of the solvent is 1% by weight.

20. Process according to claim 1, wherein the reaction temperature in step b) is 60° C. up to the boiling temperature of the solvent used at the reaction pressure, characterized in that the maximum reaction temperature is 300° C., with the reaction pressure being 0.5 to 100 bar.

21. Compounds of the formula (IV)

$$\text{(IV)}$$

in which $R^1$ and $R^2$ are each independently hydrogen, $C_1$–$C_{12}$-alkyl, $CO(C_1$–$C_{12}$-alkyl), $CO(C_5$–$C_{14}$-aryl), $CO(C_6$–$C_{15}$-arylalkyl), $COO(C_1$–$C_{12}$-alkyl), $COO(C_5$–$C_{14}$-aryl), $COO(C_6$–$C_{15}$-arylalkyl), $COO(C_2$–$C_{12}$-alkenyl) or $C_6$–$C_{15}$-arylalkyl, or $NR^1R^2$ as a whole is a cyclic radical having a total of 4 to 16 carbon atoms, or is isocyanate, and $R^3$, $R^4$, $R^5$ and $R^6$ are each fluorine or $C_1$–$C_{12}$-perfluoroalkyl, or two of the $R^3$, $R^4$, $R^5$ and $R^6$ radicals form a cyclic perfluoroalkyl radical having a total of 4 to 20 carbon atoms, and n is one or two, and $R^7$ is $C_1$–$C_{12}$-alkyl, $C_5$–$C_{14}$-aryl, $C_6$–$C_{15}$-arylalkyl, hydroxyl, chlorine, bromine, fluorine, nitro, cyano, free or protected formyl, $C_1$–$C_{12}$-haloalkyl, or radicals of the formulae (IIa) to (IIf),

| | |
|---|---|
| A-B-D-E | (IIa) |
| A-E | (IIb) |
| A-SO$_2$-E | (IIc) |
| A-B—SO$_2$R$^9$ | (IId) |
| A-SO$_3$W | (IIe) |
| A-COW | (IIf) | in which, each independently,

A is absent or is a $C_1$–$C_8$-alkylene radical and

B is absent or is oxygen, sulphur or $NR^8$, where $R^8$ is hydrogen, $C_1$–$C_8$-alkyl, $C_6$–$C_{15}$-arylalkyl or $C_5$–$C_{14}$-aryl, and D is a carbonyl group and E is $R^9$, $OR^9$, $NHR^{10}$ or $N(R^{10})_2$ where $R^9$ is $C_1$–$C_8$-alkyl, $C_6$–$C_{15}$-arylalkyl, $C_1$–$C_8$-haloalkyl or $C_5$–$C_{14}$-aryl, and $R^{10}$ is in each case independently $C_1$–$C_8$-alkyl, $C_6$–$C_{15}$-arylalkyl or $C_6$–$C_{14}$-aryl, or $N(R^{10})_2$ together is a cyclic amino radical having 4 to 12 carbon atoms and W is OH, $NH_2$ or OM where M is an alkali metal ion, half an equivalent of an alkaline earth metal ion, an ammonium ion or an organic ammonium ion, and m is an integer from 0 to 5−n and $Hal^1$ is chlorine, bromine or iodine.

22. Compounds according to claim 21, wherein formula (IV) is selected from the group consisting of 4-(1-bromo-1,1,2,3,3,3-hexafluoro-2-propyl)aniline, 2-chloro-4-(1-bromo-1,1,2,3,3,3-hexafluoro-2-propyl)aniline, 2-bromo-4-(1-bromo-1,1,2,3,3,3-hexafluoro-2-propyl)aniline, 2-fluoro-4-(1-bromo-1,1,2,3,3,3-hexafluoro-2-propyl)aniline, 2-methyl-4-(1-bromo-1,1,2,3,3,3-hexafluoro-2-propyl)aniline, 2-methyl-4-(2-bromotetrafluoroethyl)aniline, 2-methyl-4-(1-bromo-1,1,2,3,3,3-hexafluoro-2-propyl)acetanilide, 2-methyl-4-(2-bromo-1,1,1,2,3,4,4,4-octafluoro-3-butyl)aniline and 2-methyl-4-(2-bromo-1,2,3,3,4,4,5,5-octafluorocyclo-1-pentyl)aniline.

* * * * *